United States Patent [19]
Benderev et al.

[11] Patent Number: 5,749,884
[45] Date of Patent: May 12, 1998

[54] BONE ANCHOR IMPLANTATION DEVICE AND METHOD

[75] Inventors: Theodore V. Benderev, San Juan Capistrano; Neil H. Naves; Mark J. Legome, both of Mission Viejo, all of Calif.

[73] Assignee: Boston Scientific Technology, Inc., Maple Grove, Minn.

[21] Appl. No.: 345,003

[22] Filed: Nov. 23, 1994

Related U.S. Application Data

[63] Continuation of Ser. No. 862,847, Apr. 3, 1992, abandoned, which is a continuation-in-part of Ser. No. 801,747, Dec. 3, 1991, abandoned.

[51] Int. Cl.$^6$ ........................................ A61F 5/00
[52] U.S. Cl. .................. 606/167; 606/80; 606/96; 606/172
[58] Field of Search ........................... 128/883, 884; 60/29, 30, 31, 167, 172, 96, 97, 98, 79, 80

[56] References Cited

U.S. PATENT DOCUMENTS

| | | |
|---|---|---|
| 1,030,530 | 6/1912 | Palmer . |
| 2,200,120 | 5/1940 | Nauth . |
| 2,400,251 | 5/1946 | Nagel . |
| 2,454,680 | 11/1948 | Stephens . |
| 2,666,430 | 1/1954 | Gispert . |
| 2,738,790 | 3/1956 | Todt, Sr. et al. . |
| 2,809,628 | 10/1957 | Jonas . |
| 3,669,118 | 6/1972 | Colon-Morales . |
| 3,835,849 | 9/1974 | McGuire . |
| 3,842,825 | 10/1974 | Wagner . |
| 3,892,232 | 7/1975 | Neufeld ........................ 606/73 X |
| 3,995,619 | 12/1976 | Glatzer . |
| 4,156,424 | 5/1979 | Burgin . |
| 4,172,458 | 10/1979 | Pereyra . |
| 4,257,411 | 3/1981 | Cho . |

(List continued on next page.)

FOREIGN PATENT DOCUMENTS

| | | |
|---|---|---|
| 59044 | 9/1982 | European Pat. Off. . |
| 153831 | 9/1985 | European Pat. Off. . |
| 0241240 | 10/1987 | European Pat. Off. . |
| 0281763 | 2/1988 | European Pat. Off. . |
| 0440991 | 8/1991 | European Pat. Off. . |
| 2305815 | 8/1974 | Germany . |
| 2830566 | 1/1980 | Germany . |
| 2907962 | 7/1980 | Germany . |
| 3412362 | 10/1985 | Germany . |
| 1090377 | 5/1984 | U.S.S.R. . |
| 1225547 | 4/1986 | U.S.S.R. . |
| 1448111 | 9/1976 | United Kingdom ............. 606/96 |
| 2069846 | 2/1981 | United Kingdom . |
| 2252732 | 8/1992 | United Kingdom . |
| 9200773 | 1/1992 | WIPO . |
| 9310715 | 6/1993 | WIPO . |

OTHER PUBLICATIONS

*Experience with a Simplified Technique for the Treatment of Female Stress Urinary Incontinence*, by R.O. Parra and L. Shaker, British Journal of Urology 66, 615–617 (1990).

*A Simplified Surgical Procedure for the Correction of Stress Incontinence in Women* by Armand J. Pereyra, M.D., F.A.C.S. in West.J.Surg., Obst. & Gynec. Jul.–Aug., 1959.

*Marshall–Marchetti Procedure Modification* by Charles F. McKiel, Jr., et al. in The Journal of Urology 1966.

*Endoscopic Suspension of the Vesical Neck for Urinary Incontinence* by Thomas a. Stamey, M.D. in Surgery, Gynecology & Obstetrics Apr. 1973 vol. 136.

(List continued on next page.)

*Primary Examiner*—Sam Rimell
*Attorney, Agent, or Firm*—Knobbe, Martens, Olson & Bear, LLP

[57] ABSTRACT

Bone anchor implantation devices for use in the surgical treatment of stress urinary incontinence are disclosed. Methods for positioning a bone anchor implantation device over a bone and for installing a bone anchor in a bone are also disclosed.

18 Claims, 4 Drawing Sheets

U.S. PATENT DOCUMENTS

| Patent # | Date | Inventor | Class |
|---|---|---|---|
| 4,323,057 | 4/1982 | Jamieson . | |
| 4,325,373 | 4/1982 | Slivenko et al. | 606/80 |
| 4,383,527 | 5/1983 | Asnis et al. . | |
| 4,421,112 | 12/1983 | Mains et al. | 606/96 |
| 4,535,768 | 8/1985 | Hourahane et al. | 606/96 |
| 4,545,374 | 10/1985 | Jacobson | 606/84 X |
| 4,672,957 | 6/1987 | Hourahane | 606/96 |
| 4,686,972 | 8/1987 | Kurkland | 606/80 X |
| 4,708,139 | 11/1987 | Dunbar, IV . | |
| 4,713,077 | 12/1987 | Small | 623/16 |
| 4,722,331 | 2/1988 | Fox | 606/80 X |
| 4,739,751 | 4/1988 | Sapega et al. . | |
| 4,744,353 | 5/1988 | McFarland . | |
| 4,784,126 | 11/1988 | Hourahane | 606/96 |
| 4,788,970 | 12/1988 | Kara et al. | 606/80 X |
| 4,872,451 | 10/1989 | Moore et al. . | |
| 4,883,048 | 11/1989 | Purnell et al. | 606/96 |
| 4,920,958 | 5/1990 | Walt et al. | 606/96 |
| 4,945,904 | 8/1990 | Bolton et al. | 606/96 |
| 4,957,498 | 9/1990 | Caspari et al. | 606/146 |
| 4,978,351 | 12/1990 | Rozas | 606/96 |
| 4,985,032 | 1/1991 | Goble | 606/96 |
| 4,997,434 | 3/1991 | Seedhom et al. | 606/80 |
| 5,013,292 | 5/1991 | Lemay . | |
| 5,026,376 | 6/1991 | Greenberg | 606/96 |
| 5,027,793 | 7/1991 | Englehardt et al. | 606/53 X |
| 5,030,219 | 7/1991 | Matsen, III et al. | 606/53 |
| 5,108,397 | 4/1992 | White . | |
| 5,112,337 | 5/1992 | Paulos et al. | 606/98 X |
| 5,112,344 | 5/1992 | Petros . | |
| 5,116,338 | 5/1992 | Poggie et al. | 606/96 X |
| 5,141,513 | 8/1992 | Fortune et al. | 606/96 |
| 5,152,764 | 10/1992 | Goble | 606/98 X |
| 5,163,940 | 11/1992 | Bourque . | |
| 5,203,784 | 4/1993 | Ross et al. . | |
| 5,207,753 | 5/1993 | Badrinath | 606/96 |
| 5,256,133 | 10/1993 | Spitz . | |
| 5,372,146 | 12/1994 | Branch . | |
| 5,611,515 | 3/1997 | Benderev et al. . | |

OTHER PUBLICATIONS

*Modified Bladder Neck Suspension For Female Stress Incontinence* by Shlomo Raz, M.D. in Urology Jan. 1981 vol. XVII, No. 1.

*Peripubic Urethropexy For Urinary Stress Incontinence in Women* by Chester C. Winter, M.D. in Urology Oct. 1982 vol. XX, No. 4.

*Female Urinary Incontinence* by George D. Webster in Urologic Surgery 3rd Edition 1983.

*A Comparison of Endoscopic Suspension of the Vesical Neck with Suprapubic Vesicourethropexy for Treatment of Stress Urinary Incontinence* by Julia R. Spencer et al. in The Journal of Urology vol. 137 Mar. 1987.

*No–Incision Pubovaginal Suspension for Stress Incontinence* by Ruben F. Gittes et al. in the Journal of Urology vol. 138 Sep. 1987.

*Bone Fixation Technique for Transvaginal Needle Suspension* by Gary E. Leach, M.D. in Urology vol. XXXI No. 5 May 1988.

*Review of an 8–Year Experience with Modifications of Endoscopic Suspension of the Bladder Neck for Female Stress Urinary Incontinence* by Kevin R. Loughlin et al. in The Journal of Urology vol. 143 Jan. 1990.

*The Sling Procedure for Urinary Stress Incontinence* by Edward J. McGuire, M.D. in Profiles in Urology undated.

M.S. Henderson, Bone Surgery Instruments, p. 7. Sep. 4, 1937.

*Therapy of Urinary Stress Incontinence in Women Using Mitek® GII Anchors* by Valenzio C. Mascio, M.D.

*The Sling Procedure for Urinary Incontinence* by Edward J. McGuire, M.D., in Profiles in Urology.

BONE ANCHOR IMPLANTATION DEVICE AND METHOD

This application is a continuation of application Ser. No. 07/862,847, filed Apr. 1, 1992 now abandoned; which is a continuation-in-part of application Ser. No. 07/801,747, filed Dec. 3, 1991, now abandoned.

BACKGROUND OF THE INVENTION

The present invention relates to the treatment of stress urinary incontinence "SUI," and, in particular, to improved methods and surgical devices for the surgical treatment of SUI in females. The devices disclosed herein are additionally useful in a wide variety of other surgical procedures.

Genuine stress incontinence is the involuntary loss of urine due to a sudden rise in intra-abdominal pressure. It has been estimated that between 40% and 50% of young, healthy nulliparous women admit to occasional mild stress incontinence; however, at least 80% of stress incontinence patients are in the perimenopausal age group and are multiparous. Raz[3] has suggested that the female urethral continence mechanism is dependent on the interaction of four urethral factors: urethral closing pressure, urethral length, urethrotrigonal anatomy, and urethral reception of intra-abdominal pressure.

The urethral closing pressure is predominantly a result of the interaction of smooth and striated muscle sphincter activity, but there is also some contribution by nonmuscular urethral factors such as the submucosal vascular plexus, the elastin and collagen content of the urethral tissues, and a sphincter like effect of the mucosa. There has been considerable diversity of opinion regarding the anatomic structure and the innervation of the urethral sphincters, and a variety of views have been expressed in the literature.

Lapides and associates have stressed the importance of urethral length in the maintenance of continence in the female. However, although it certainly interacts with other factors to contribute to continence, a short urethra alone will not produce incontinence. Urethral length varies considerably in normal women, and women with proven genuine stress urinary incontinence do not invariably have urethral shortening.

Urethrotrigonal anatomy, which can be demonstrated by lateral cystourethrography, should fulfill certain criteria. The bladder base should lie above the level of the inferior ramus of the symphysis, and with straining should not descend more than 1.5 cm. There should be a normal urethrotrigonal alignment with an angle normally less than 100 degrees, and the urethral axis should be approximately 35 degrees from the vertical. In the hypermobile situation loss of all of the normal anatomic features may occur, a radiologic finding that correlates with the clinical finding of cystourethrocele. However, clinical experience has shown that the coexistence of cystourethrocele and incontinence does not predict that the incontinence is of a genuine stress variety.

The transmission of intra-abdominal pressure to the intra-abdominal portion of the proximal urethra is also reported to be important in the maintenance of continence. This is a passive phenomenon, and is the result of the normal anatomic configuration just described. Whenever there is a rise in intra-abdominal pressure during such stresses as coughing or straining, the pressure is transmitted not only to the bladder but also to the proximal urethra, with resultant increase in the closing pressure, and prevention of leakage. If the urethral axis is altered, rotational descent will drop the proximal urethra and bladder base from its intra-abdominal location, and will obviously impair such pressure transmission.

A wide variety of operations have been used to correct this condition, generally involving the principles of elevating the bladder neck anteriorly and/or elongating and narrowing the proximal urethra. Two of the most popular operations today for female stress incontinence are the Marshall-Marchetti-Krantz and Birch vesicourethropexies. The Marshall-Marchetti-Krantz technique has at least an eighty-five percent success rate, against which other operative success rates must be measured. Recently, the Pereyra operation and its modifications have enjoyed some popularity, but less than basic techniques.

Notwithstanding the foregoing, however, there remains a need for an improved treatment for SUI. Preferably, the treatment is as noninvasive as possible under the circumstances, and will eliminate or minimize hospitalization and the use of general anesthetics. In addition, there remains a need for improved medical instrumentation such as drill guides and suture passers for use in connection with SUI treatment and other medical procedures.

SUMMARY OF THE INVENTION

There is provided in accordance with one aspect of the present invention a drill guide for directing a drill bit at a selected site on a bone. The drill guide comprises a housing, and at least two chambers extending axially within the housing. Each of the chambers has an opening at the distal end. A plunger is provided in each of the chambers, each plunger axially movable from a first retracted position to a second extended position. A probe is mounted on the distal end of each of the plungers, and adapted for retraction within the open end of the chamber and extension outside of the open end of the chamber. In a simplified embodiment, each of two or more probes is axially movably disposed within the housing, without the use of a distinct plunger. A drill guide channel extends axially through the housing, within a plane parallel to the plane joining the axes of the first and second chambers, and in between the axes of the first and second chambers.

Preferably, one or both of the plungers is provided with a releasable lock for releasably retaining the plunger in the retracted position, thereby minimizing the likelihood of accidental needle sticks. The preferred probe comprises a hypodermic needle or a sharpened solid wire. In a two probe embodiment, the axes of the first and second probes are separated by a distance within the range from about 5 mm to about 15 mm. Preferably, the axis of the drill guide channel is approximately equidistant from the axes of each of the probes.

In accordance with another aspect of the present invention, there is provided an alternate embodiment of a drill guide for use in locating drill sites in a patient's body. The drill guide comprises a body, a handle connected thereto, and one or more bores extending through said body. Each bore has an opening at a distal end. A probe is provided in each bore, the probe being axially movable from a retracted to an extended position. A drill guide bore, which may also act as one of the probe bores, extends axially through the body. A suture slot extends from outside of the body to the drill guide bore along the length of the body. Serrations are provided on the distal end of the body, aiding in maintaining the opening of a drilled hole. In a two probe embodiment, the axes of the probes are separated by a distance of about 5 to 10 mm. Preferably, the probes of this embodiment are a unitary element, such as a wire or needle. Further, it is desired that the drill guide bore and any probe bores lie in a line perpendicular to the longitudinal axis of the body.

In accordance with the further aspect of the present invention, there is provided a method of positioning a drill guide over a drilling site on bone, comprising the steps of providing a drill guide of the type having a housing, at least two axially extendable probes within the housing, and a drill guide extending through the housing. A first probe is extended from the retracted position to the extended position, and advanced through the tissue until it contacts a bone. The second probe is thereafter extended from the retracted position to the extended position, until the second probe contacts the bone. If the first extension of the second probe does not result in a contact, both probes are retracted within the housing, and the drill guide is translated along the sagittal or other axis. The first probe is thereafter reextended and the foregoing steps are repeated until both the first and second probes contact the bone.

In accordance with another aspect of the present invention, there is provided a method of installing a bone anchor in a bone, utilizing the drill guide defined above. In accordance with the installation method, each of the probes is sequentially extended and advanced through tissue as described until each of said probes is in contact with the bone. A drill bit is thereafter advanced through the drill guide channel and a hole is drilled in the bone. The drill bit is thereafter withdrawn from the drill guide channel, and a suture anchor is advanced through the drill guide shaft and into the bone.

In accordance with another aspect of the present invention, there is provided a bladder neck suspension procedure involving use of the suture supports, anchors, and the "C" clamp or drill guide or suture passer.

In accordance with this procedure, the drape and exposure system are prepared on the patient as before. The suture passer is passed through an incision made over the pubic bone into the vagina. A suture that is attached to a suture support is captured in the suture channel of the passer at the other. The passer is passed back out of the patient, until the suture is pulled slightly taut. The free end of the suture is then affixed to the pubic bone with a knot, plug, or anchor. The anchor may be placed by pressing it into a hole drilled into the bone, as located by the "C" clamp or drill guide.

Alternatively, the drill guide or "C" clamp may be used to position a drill bit for drilling a passageway from the pubic area to the vagina. The free end of the suture is then passed through the drilled hole up from the vagina to the pubic area. The free end of the suture may then be tied off or affixed by a plug or anchor to prevent it from pulling back through.

In accordance with a further aspect of the present invention, there is provided a surgical bladder neck suspension procedure, for the treatment of stress urinary incontinence. In accordance with the method, a technique of creating a suspension web comprising a plurality of lengths of suture is constructed extending between the pubocervical fascia and the pubic bone, on each of the right and left sides of the midline. Sutures are carried through tissue utilizing the suture passer disclosed herein, and sutures are tied down to the pubic bone utilizing a bone anchor positioned on each of the right and left sides of the midline by a drill guide as disclosed herein. Prior to tying, sutures are appropriately tensioned by advancing the suture around the suture tensioner disclosed herein and tying in a conventional manner. Thereafter, the suture tensioner is removed and the surgical site prepared and closed in a conventional manner.

These and additional features and advantages of the present invention will become apparent from the detailed description of preferred embodiments which follows, when taken together with the attached drawings and claims.

DETAILED DESCRIPTION OF PREFERRED EMBODIMENTS

SUI is generally curable with any of a variety of surgical procedures that properly suspends the bladder neck. However, limitations of known procedures include 1) the extent of surgical morbidity 2) the ever present threat of long term failures and 3) the reproducibility between different surgeons.

Pereyra[1] introduced the transvaginal bladder neck suspension as a less invasive alternative to open retropubic procedures. Stamey[2] limited morbidity and improved the reproducibility of the transvaginal bladder neck suspension by introducing endoscopic control and confirmation of suture placement. Raz[3] has improved reproducibility by introducing full palpatory control of needle passage through the retropubic space, thereby limiting disability through injury to the bladder or other retropubic structures.

The distal passage of the suture passer disclosed herein or other needle followed by a sweep back to the bladder neck area described herein accomplishes a similar goal but without the necessity of entering the retropubic space. Passage of the needle point to the level of the introitus along the underside of the pubic bone obviates the need to turn the needle down toward a bladder neck that has been digitally elevated, thereby reducing the risk of bladder injury. Extraction of the needle from the pubourethral ligament is necessary to allow a "capture" of the more pliable pubocervical fascia alongside the urethra. The subsequent, gentle sweep back of the needle along the surface of the pubocervical fascia provides an easy and safe means of introducing the needle to the bladder neck area under the vaginal digital guidance.

Gittes and Loughlin[5] have further popularized the technique of Pereyra and demonstrated an advantage of increased long-term efficacy by creating an autologous bolster with the transvaginal passage of a curved needle. As an alternative manner of creating an autologous bolster, the proposed modification described herein uses the suture passer disclosed herein, or a Stamey needle through a suprapubic approach to carry the suture through all of its vaginal passes. The full carriage of the suture by the suture passer needle offers the benefits of 1) improving accuracy and reproducibility by allowing palpation of the needle at each vaginal entry point in reference to the bladder neck and catheter, 2) potentially decreasing morbidity by reducing the risk of injury and/or irritation through inadvertent entry into any part of the urethra or bladder and 3) possibly contributing to long term efficacy by assuring that a full thickness layer of pubocervical fascia is captured. This technique permits the capture of a large lateral volume of pubocervical fascia similar in an area to that available for suturing in an open retropubic urethropexy.

Leach[4] has limited morbidity by decreasing post-operative pain and has potentially improved long-term efficacy with pubic fixation of the suspending sutures. However, the trochar needle passage through the pubic bone as described by Leach can be difficult through the limited exposure that is used with some forms of endoscopic bladder neck suspension. Other various forms of pubic bone fixation have also been described with transvaginal and open bladder neck suspension surgery[6,7,8]. To facilitate the anchoring of the suspensory suture to the pubic bone with minimal soft tissue dissection, the present inventor has used a new set of devices called the Mitek Anchor System. The latest generation of Mitek anchor, the G2, consists of a titanium body coupled to nickel-titanium arcs. These anchors have recently been used most commonly for tenodesis and ligamentous reconstruction of the shoulder and foot[9,10].

In the present setting of bladder neck suspensions, the Mitek anchor with attached suture is passed into a hole drilled in the pubic bone. Care must be taken to assure that the hole has been drilled into the pubic bone and not inferiorly through the tendon of the adductor longus or superiorly through the rectus fascia over the surface of the pubis. Proper location of the drill and placement of the bone anchor in the bone is facilitated by the drill guide illustrated in FIGS. 1–4 and discussed infra.

Once the anchor is passed into the bone, the anchor's unique memory forces the arcs to spring open to their original shape and to engage in the cancellous portion of the pubic bone. The complication of infection with use of the anchor has not been noted, which may, in part, be due to the emphasis on broad spectrum antibiotics and sterile technique with use of video endoscopy, when possible.

Anchor pubic bone fixation in one study by the inventor herein was associated with a limitation of post-operative pain allowing the procedure to be performed on an outpatient basis in many of the patients. Pubic anchor fixation may limit suspending suture pull through at the level of the rectus fascia. Any assessment of resultant improvement of long term efficacy will require longer follow-up.

In accordance with one aspect of the present invention, there is provided a drill guide for locating drill sites inside a patient's body. More specifically, the invention relates to a multi-probe bone locator and drill guide centering device for locating a desired site on a bone, guiding a drill bit to the located site, retaining access to the site following drilling, and installation of a bone anchor for anchoring sutures.

Figures 1, 2:
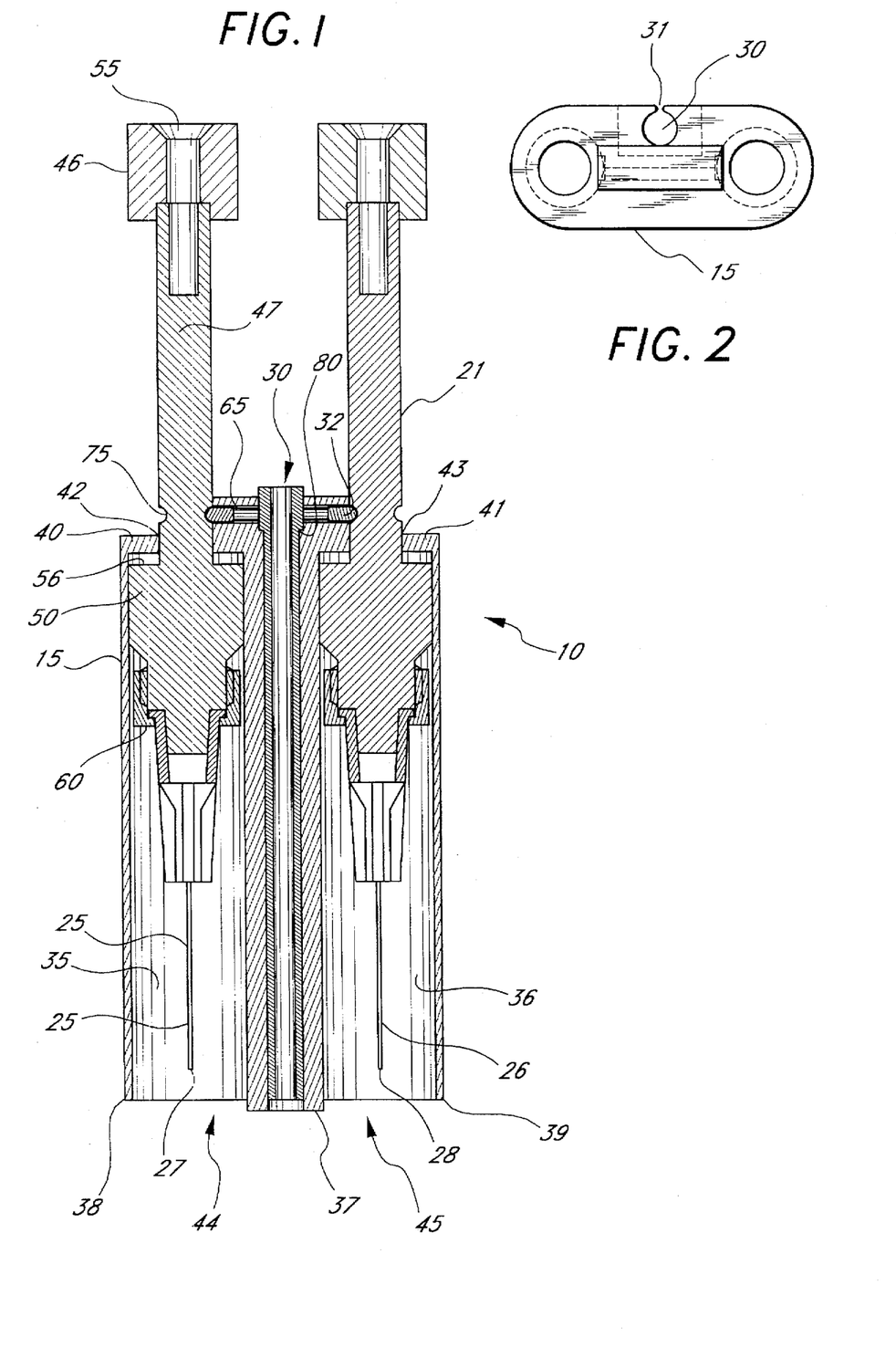
FIG. 1 is an elevational partial cross sectional schematic view of a drill guide in accordance with the present invention.
FIG. 2 is an end view of the drill guide of FIG. 1.

Referring to FIG. 1, there is shown a surgical drill guide 10 in accordance with one aspect of the invention. Generally, drill guide 10 comprises a body 15 carrying two or more plungers 20, 21, each having a bone probe 25, 26 at its end. A guide shaft 30 is located between two adjacent bone probes 25, 26. Alternatively, one or more of the plungers 20, 21 can be eliminated, so that one or more probes 25, 26 is directly mounted within or to body 15. Thus, in a simplified design, a drill guide channel is held in proximity to two or more elongate probes such as hypodermic needles which are preferably axially movable.

Body 15 is the support structure for the drill guide 10. The body 15 may have any of a variety of exterior configurations; however, it is preferred that the body be sufficiently axially elongate to facilitate withdrawal of the sharpened distal tips 27, 28 of the probes 25, 26 therein to minimize accidental needle sticks, and generally oval or rectangular in cross section. See, e.g., FIG. 2. The inside of the body 15 has two or more identical chambers 35, 36 spaced apart from each other to accommodate a drill guide shaft 30, as will be discussed. Preferably, an annular tissue compression portion 37 of body 15 adjacent the guide shaft 30 extends slightly farther in the distal direction than the lateral sidewalls 38, 39 of the body 15. Tissue compression portion 37 is optimally provided with a rough or serrated edge surface for contacting the tissue surrounding the drill site as will be discussed.

Each chamber 35, 36 extends from the distal end of the body 15 to a point near the proximal end of the body 15. In this manner, chambers 35, 36 are provided with open distal ends to permit reciprocal axial motion of the bone probes 25, 26 therethrough. Proximal ends of chambers 35, 36 are provided with a stop such as end walls 40, 41 having central passageways 42, 43 therethrough for movably accepting the plungers 20, 21. Similarly, distal ends 44, 45 of chambers 35, 36 can be provided with an end wall (not illustrated) having a probe opening therein, or a pierceable septum for permitting passage of probes 25, 26 therethrough.

The exact distance between the axes of adjacent chambers 35, 36 depends on the procedure for which the device is to be used. For example, in a bladder neck suspension procedure, the axes of chambers 35 should be separated by a distance of no more than about 10 mm from their centerlines, in an embodiment having coaxial probes and plungers, so that the corresponding probe separation is also no more than about 10 mm. Preferably, the separation between adjacent probes is within the range of from about 5 mm to about 15 mm.

Due to the bilateral symmetry of the illustrated embodiment, only one side will be particularly described below. The plunger 20 preferably comprises three main portions: an engaging knob 46, a main shaft 47 and a stop 50. The knob 46 is generally a cylindrical body attached to the top of the shaft 47 and shaped for easy engagement with a thumb or hand. This knob 46 may be attached to shaft 47 in a variety of manners. For example, knob 46 is illustrated as having a recessed portion on its distal surface for accepting the proximal end of shaft 47. A screw 55, preferably flat headed, is then passed through the top of the knob into the top of the shaft 47 to securely lock them together. Alternatively, the shaft 47, knob 46 and stop 50 can be integrally molded from any of a variety of thermoplastic materials well know in the art of surgical instrument manufacturing.

The plunger shaft 47 extends from the knob 46 through the opening 42 in the proximal end wall 40 of the body 15 and into chamber 35. Shaft 47 preferably is at least about 25 mm long from the distal surface of the knob 46 to the proximal surface of end wall 40 on body 15. In this manner, the plungers 20, 21 have a sufficient range of axial travel between a first, retracted position in which the distal tips 27, 28 of probes 25, 26 are shielded, and a second, extended position in which the distal tips 27, 28 of probes 25, 26 are exposed. It is contemplated, however, that the length of the shaft 47, probe 25 and axial travel may vary depending on the intended procedure.

A stop 50 is positioned on the distal end of the shaft 47. The stop 50 and shaft 47 may either be separately fabricated or may be fashioned from one piece of material such as by known molding or lathing techniques. The illustrated stop 50 comprises a radially outwardly extending portion of the plunger 20 which travels within the chamber 35 to produce a transverse abutment surface 56. The stop 50 thus limits the proximal range of travel of the plunger 20 by engagement of the abutment surface 56 with the distal surface of end wall 40 of the body 15. The stop 50 is preferably provided at its distal end with a connector such as a standard luer for attachment of a probe 25. As will be appreciated by one of skill in the art, any of a wide variety of interlocking or complementary surface structures can be devised to accomplish the function of stop 50.

In the illustrated embodiment, the probe 25 is inserted into a threaded cap 60. This cap 60 is preferably threaded on its interior surface so that it may be attached to the correspondingly threaded distal end of stop 50. Alternatively, the probe 25 can be connected to the stop 50 or shaft 47 such as by molding the proximal end of the probe 25 therein.

Each probe 25, 26 extends from the corresponding shaft 47 towards the distal end of the chamber 35. Probe 25 may comprise standard hypodermic tubing such as a standard needle, or a solid wire probe preferably having a sharpened distal end.

The length of the probe 25 is preferably such that when the plunger 20 is in a fully retracted state, the distal end of the probe 25 is spaced by at least about 4 mm from the open distal end of the chamber 35. In this manner, the probe end is protected against contamination and the user of the drill guide 10 is protected against accidental probe sticks. Alternatively, the probes 25, 26 can be rigidly secured to the body 15 or directly to a tubular drill guide shaft 30 as will be apparent to one of skill in the art.

In an embodiment having axially movable plungers, the plunger 20 is normally retracted proximally such that the distal tip 27 of probe 25 connected thereto is recessed from the distal end 44 of the chamber 35. This position is preferably releasably maintained by engaging rods 65 which are biased in the direction of annular recess 75 in the shaft 47 of the plunger 20.

In the illustrated embodiment, annular recess 75 is provided in the plunger shaft 47 at a point adjacent the proximal end of the body 15. When the plunger 20 is retracted, recess 75 releasably receives rod 65. This rod 65 is biased such as by a spring so that it provides an interference fit within recess 75 and holds the plungers 20 in their retracted position. The rods 65 and springs are preferably mounted within a housing adjacent the proximal end of the body 15.

A drill guide shaft 30 extends axially in between the two chambers 35, 36 containing the plungers 20, 21. Preferably, drill guide shaft 30 is disposed approximately equidistant from the longitudinal axis of each of chambers 35, 36 so that when each of the probes 25, 26 is in contact with a bone, the axis of drill guide shaft 30 will be spaced well away from the edge of the bone. In addition, in the illustrated embodiment, the axis of shaft 30 is offset laterally from the plane connecting the axes of chambers 35 so that the axes of the two probes and the drill guide shaft 30 are disposed on vertices of a triangle. See FIG. 2. This configuration facilitates the use of a slot 31 extending the length of guide shaft 30 for receiving a suture during the installation of the suture anchor.

Drill guide shaft 30 is optionally surrounded by an elongate tubular bushing 80 extending throughout at least a portion of the body 15, and preferably positioned so that the distal end of the bushing 80 is slightly recessed from the distal portion 37 of body 15. This bushing 80 aids in properly centering a later installed drill bit and acts as a channel through which a suture anchor is introduced into the hole after drilling.

Figure 3:
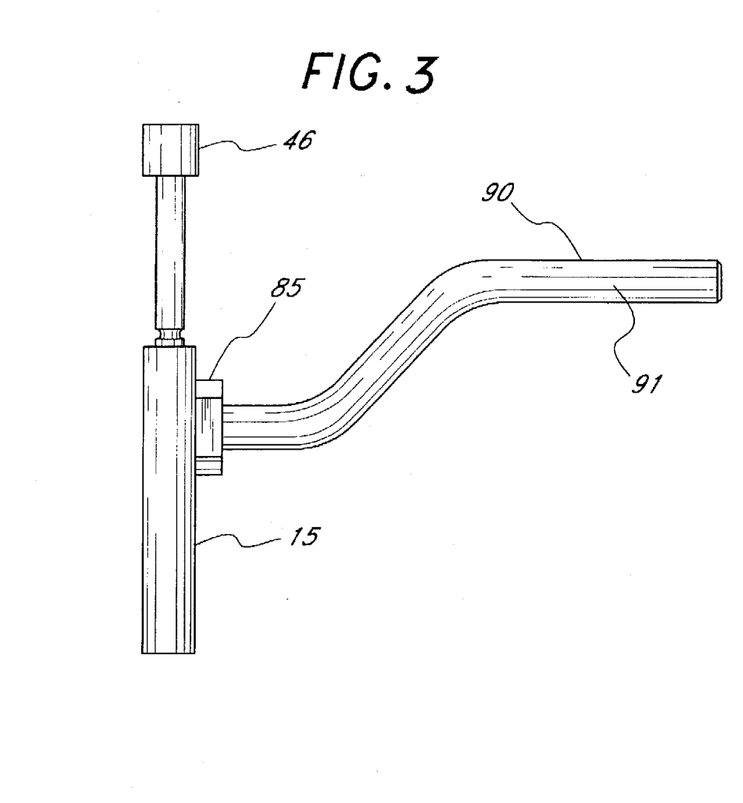
FIG. 3 is a side elevational schematic view of the drill guide of FIG. 1.
Figure 4:
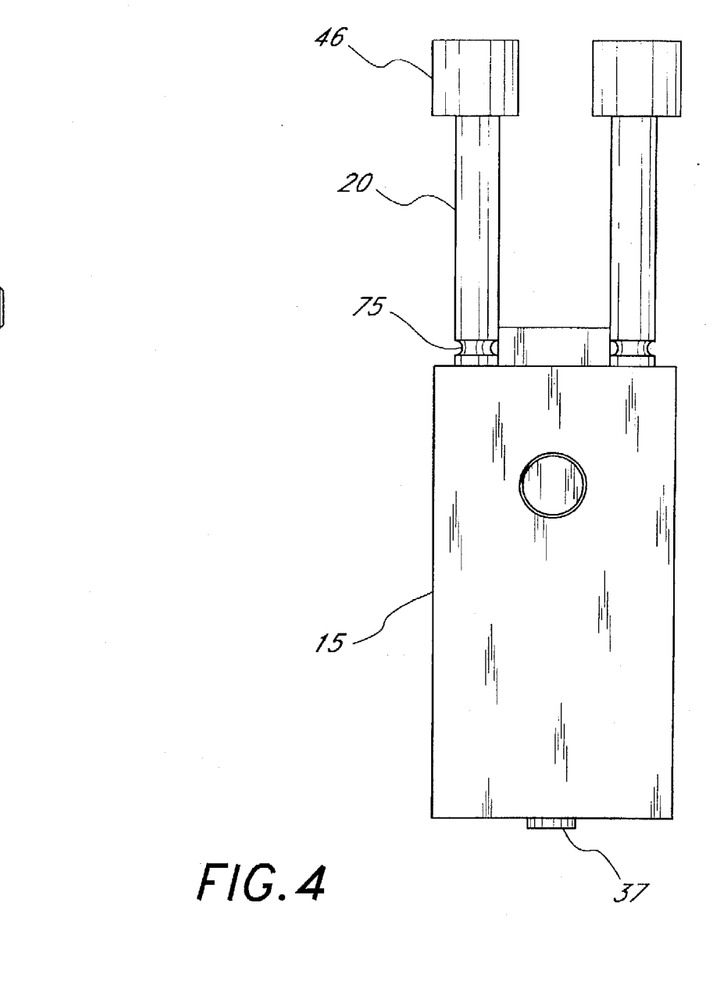
FIG. 4 is a front elevational view of the drill guide shown in FIG. 3.

Referring to FIG. 3, there is disclosed a handle 90 connected to the outside of the body 15 for maneuvering the drill guide 10. This handle 90 is preferably generally tubular in shape, and approximately 10 mm in diameter for easy gripping by the user. The handle 90 as illustrated extends from its connection with the body 15 laterally away from said body, then upward and outward at an angle, and finally ends in a gripping section 91 which extends generally along a perpendicular to the axis of the body 15. This handle design permits the user to forcefully press the drill guide 10 against the body, as well as to facilitate controlled translation of the drill guide along a sagittal axis.

The handle 90 may be connected to the body 15 in any of a variety of conventional manners. In the illustrated embodiment, the handle extends into a small recess in the body 15 and then is locked in place such as with a nut 85. The nut 85 as illustrated has a threaded portion for engaging the body, and a locking portion for pushing the handle 90 into the body 15. Alternatively, the handle 90 can conveniently be integrally molded with body 15, or secured thereto such as by thermal or solvent bonding techniques or by adhesives well known in the art.

It is preferred that the components of the drill guide 10 be made of a material which is sterilizable, relatively rigid and biocompatible, such as stainless steel or any of a variety of polymers conventionally used for medical instruments of the type designed to enter the sterile field.

The operation of the surgical drill guide 10 will now be described. When it is desired to locate a bone for attachment of a suture anchor therein, the drill guide is placed on the body over the area of the bone. The drill guide 10 is centered after visualization or digital palpation over the bone.

The user pushes one or both of the knobs 46 to distally extend at least a first probe 25. The probe 25 is extended into the body by pushing the plunger 20 down, until either the plunger has been fully extended or the bone is contacted.

If the plunger extends fully without the probe contacting the bone, the probe is retracted and drill guide 10 is then repositioned for another attempt at locating the bone.

When the first probe 25 does engage the bone, pressure is released from the knob 46. The user then extends the second probe 26 by pushing on the corresponding knob of the second plunger 20. Once again, the second probe 26 will either engage the bone or the plunger 20 will fully extend without contact. If no contact is made by the second probe 26, both probes 25, 26 are retracted again by pulling upward on the appropriate knob. The drill guide 10 may then be translated along the sagittal axis and one or both probes reextended.

This process is continued until both probes 25, 26 contact the bone. At this time, the user will be assured that the bone has been located and that the guide shaft 30 is properly centered over the bone.

A drill bit is then extended through the drill bushing 80 and into the patient. The drill bit is used to drill through adjacent tissue and produce a small hole in the bone. Preferably, a step drill or other limiting structure is utilized for producing a hole having a predetermined and reproducible depth into the bone. For installation of the preferred Mitek G2 anchors disclosed herein, a 2.5 mm diameter drill bit is used to produce a hole of 15 mm depth into the bone.

The desirability of having a tissue compression portion 37 which extends distally slightly beyond the distal end of the adjacent body is now apparent. At the time the drill bit is retracted, the hole drilled would normally close upon itself because of the resiliency of the surrounding tissue. However, by maintaining pressure on the body 15 in the direction of the bone, the tissue compression portion 37 tends to compress the adjacent tissue thereby minimizing migration and maintaining the hole open.

In this manner, the tissue located directly under the guide shaft is prevented from closing, and the anchor can be readily advanced through guide shaft 30 and into the bone. Even without distally extending tissue compression portion 37, installation of the anchor is greatly simplified using the drill guide of the present invention because the axis of drill guide shaft 30 remains directed at the drill hole.

Following retraction of the drill bit, a suture anchor is advanced into the body through the drill bushing 80 and then connected within the hole in the bone. An installation tool which facilitates holding the anchor body by means of an interference fit at the gripping point and guiding said anchor through the guide hole and compressed tissue into the bone hole is preferably utilized. The suture, typically previously connected to the anchor, is permitted to trail out through the slot 31 provided for that purpose.

Referring to FIGS. 5-9, there is shown an alternative embodiment of a drill guide for use in locating drill sites inside a patient's body. As illustrated, the drill guide 210 comprises a body 215 carrying one or more probes 225, 226. A drill guide bore 230 is preferably located between the bone probes 225, 226.

Figures 5, 6:
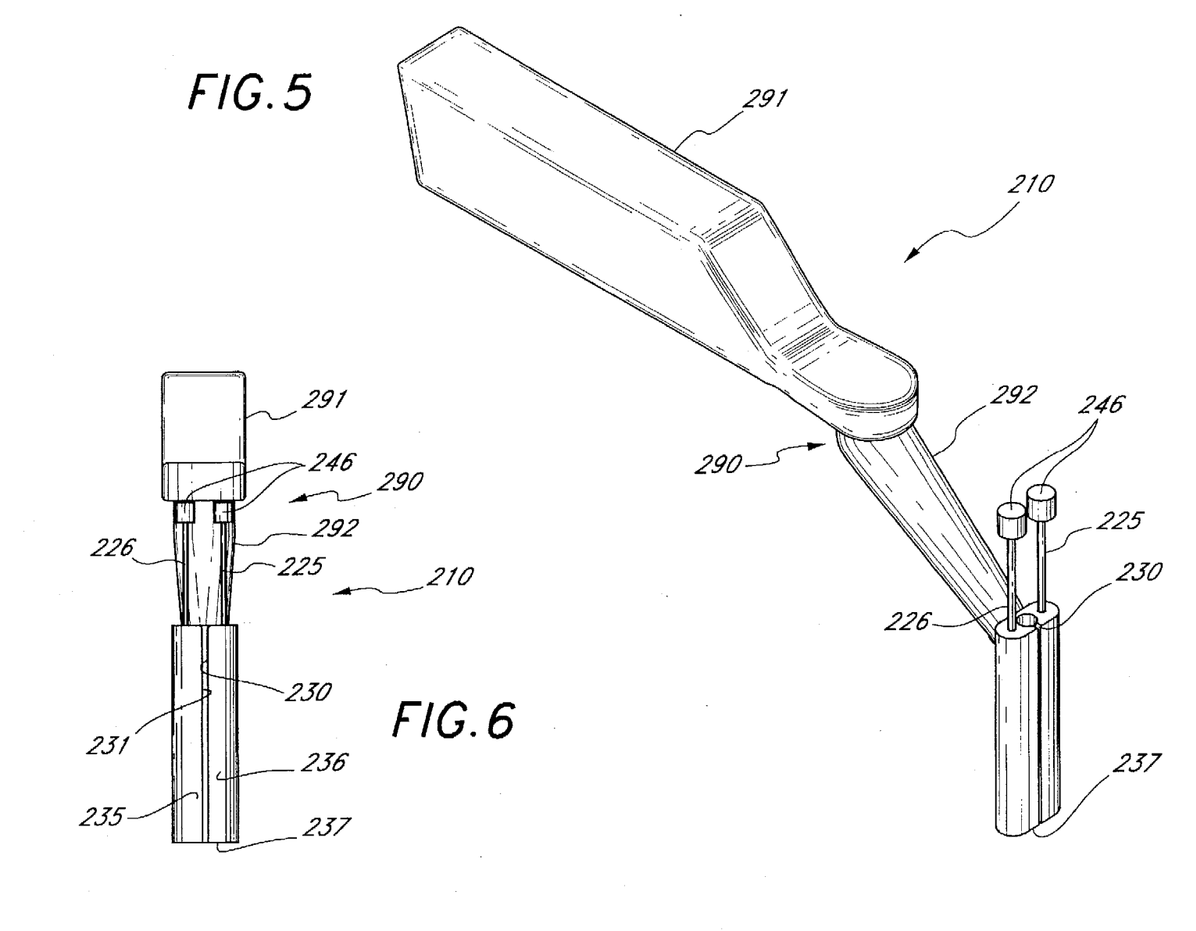
FIG. 5 is a perspective view of an alternate embodiment drill guide of the present invention.
FIG. 6 is a front elevational view of the drill guide of FIG. 5.

The body 215 is the support structure for the drill guide 210. The body 215 may have any of a variety of exterior configurations; however, it is preferred that the body be sufficiently axially elongated to facilitate withdrawal of the sharp distal tips 227, 228 of the probes 225, 226 therein to minimize accidental needle sticks. Body 215 is generally oval or rectangular in cross section.

Body 215 is provided with one or more bores 235, 236 extending therethrough (FIG. 6). As illustrated, the bores 235, 236 are spaced apart from each other to accommodate a drill guide bore 230. It is contemplated that the drill guide bore 230 may coincidentally be one of the bores 235, 236, in which case the spacing between bores 235, 236 can be reduced. If only one probe 225 is used, there may only be one bore 235, and this bore 235 may coincidentally be the drill guide bore 230 also.

Figures 7, 8, 9:
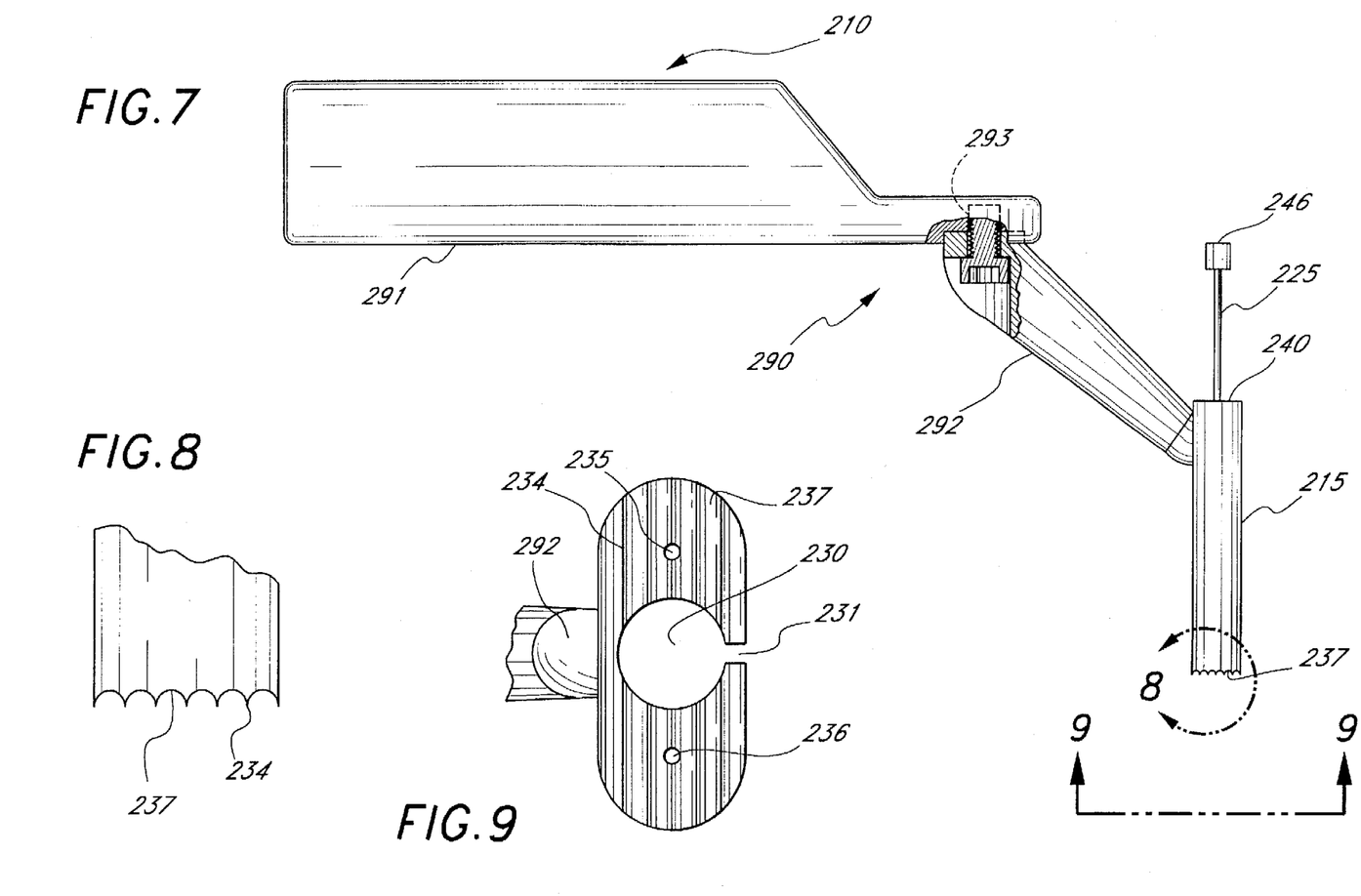
FIG. 7 is a side view with a partial cross section of the drill guide of FIG. 5.
FIG. 8 is an enlarged side view of the end of the drill guide of FIG. 7.
FIG. 9 is an enlarged end view of the drill guide of FIG. 7.

Preferably, the distal end 237 of the body 215 is provided with a number of serrations 234 (FIGS. 8 and 9). In the illustrated embodiment, serrations 234 are located approximately 1 mm apart and run generally parallel to the longest dimension longitudinally across the face of distal end 237. The serrations 234 are sharp ridges formed between curved grooves which have a diameter of about 0.5 mm and extend into the face of the distal end 237.

The exact distance between the axes of the adjacent bores 235, 236 depends on the procedure for which the device is to be used. As illustrated in FIG. 9 and as used in a bladder neck suspension technique, the axes of the bores 235, 236 should be separated by a distance of no more than about 9 mm between centerlines. In this manner, the corresponding probe separation in a two probe embodiment is also no more than about 9 mm. While this is the preferred separation distance, it is also possible for the separation to be anywhere within the range of between about 5 mm and about 10 mm.

Each probe 225, 226 preferably comprises a unitary element such as a wire or needle. An engaging knob 246 is mounted to the proximal end of each probe 225, 226. Knob 246 is a generally cylindrical body which is shaped for easy engagement with a thumb or hand. Knob 246 may be attached to the probes 225, 226 in any of a variety of manners well known in the art. As illustrated, the knob 246 is stainless steel, but may be molded from a thermoplastic material, and provided with a recess for receiving the top of the corresponding probe 225, 226.

The probes 225, 226 extend distally from each knob 246 and into the body 215 through the bores 235, 236. The probes 225, 226 are preferably at least approximately 75 mm long from the distal surface of the knobs 246 to their tips 227, 228. In addition, the axial length of the body 215 is within the range of from about 50 mm to about 60 mm long, and preferably about 50 mm long. The probes 225, 226 thus have a sufficient range of axial travel between a first retracted position in which the distal tips 227, 228 of the probes 225, 226 are shielded inside the bores 235, 236, and a second extended position in which the distal tips of the probes are exposed. It is contemplated, however, that the length of the probes 225, 226 and axial travel may vary depending on the intended procedure.

The knobs 246 act as limits on distal travel of the probes 225, 226, by engagement with the proximal surface of the end wall 240 of the body 215.

The length of the bores 235, 236 is preferably such that the distal tips 227, 228 of the probes 225, 226 are spaced by at least about 3 mm from the open distal end of the bores 235, 236 at the distal end 237 of the body 215 when the probes are retracted. In this manner the probe end is protected against damage, and the patient and user of the drill guide 210 are protected against accidental probe sticks.

Probes 225, 226 are preferably provided with a means for providing a bias in the proximal direction, to releasably retain the probes in the retracted state when not in use. In addition, sufficiently strong biasing means can assist in retraction of the probe from body tissue. The bias may be provided in any of a variety of ways known in the art such as with the use of coil springs. Preferably, a tapered conical section (not shown) is provided on the body of the probes 225, 226. A matching tapered step (not shown) is provided in each bore 235, 236. The conical section and step are arranged to engage each other so that the probes 225, 226 are maintained in a retracted state during non-use because of friction. The probes 225 and 226 may easily be released upon light finger pressure on the knobs 246. Alternatively, any of a variety of releasably retention structures for opposing a bias may be utilized as will be apparent to one of skill in the art.

As illustrated in FIGS. 5, 6 and 9 a drill guide bore 230 extends axially in between the bores 235, 236 which contain the probes 225, 226. Drill guide bore 230 in the illustrated embodiment is essentially coplanar with bores 235, 236. However, depending upon the desired diameter of drill guide bore 230 and spacing of bores 235, 236, drill guide bore 230 can be offset from the plane of bores 235 and 236. In general, the minimum diameter of drill guide bore 230 is set by the desired drill bit size and by the desired bone anchor, as has been previously discussed. Typical bone anchors of the type used herein are on the order of 2 mm in diameter.

Preferably, the drill guide bore 230 is disposed approximately equidistant from the longitudinal axis of each of the bores 235, 236 so that when each of the probes 225, 226 is in contact with a bone, the axis of the drill guide bore 230 will be spaced well away from the edge of the bone. In addition, the drill guide bore 230 preferably has a slot 231 extending the length of the guide bore 230 for receiving a suture, and for removing the drill guide after an anchor and suture have been installed.

As illustrated in FIG. 7, a handle 290 is connected to the outside of the body 215 for maneuvering the drill guide 210. The handle 290 preferably comprises two sections: a gripping portion 291 and an attachment portion 292. The attachment portion 292 extends from its connection with the body 215 upward at an angle of about 45 degrees to its connection with the gripping portion 291 which extends generally along a line perpendicular to the axis of the body 215.

The attachment portion 292 can be connected to the body 215 in any of a variety of conventional manners. In the illustrated embodiment, the attachment portion 292 is brazed to the outside of the body 215. The attachment portion 292 could alternatively be integrally molded with the body 215, or it could be otherwise secured to the body 215 by conventional welding, solvent, thermal or adhesive bonding techniques, or fastened with screws or the like.

The gripping portion 291 is preferably approximately 140 mm in length and about 20 mm wide. The gripping portion is about 30 mm thick throughout most of its length, however, near its connection with the attachment portion 291 it tapers at approximately a 45° angle to a thin section of 10 mm thickness and 30 mm length which acts as a thumb rest for the user.

The gripping portion 291 is preferably rotatable about an axis which is perpendicular to the axis of the probes 225, 226. The gripping portion 291 is thus, as illustrated, mounted on a pin 293 which extends from the bottom surface of the attachment portion 292 into a matching hole in the gripping portion 291 and clamped with a centrally located screw.

It is preferred that the components of the drill guide 210 as embodied be made of a material which is sterilizable, relatively rigid and biocompatible, such as stainless steel or any of a variety of polymers conventionally used for medical instruments of the type designed to enter the sterile field.

The operation of drill guide 210 is the same as that described for the embodiment illustrated in FIGS. 1–4. Operation of the single probe embodiment (not illustrated), will be apparent to one of skill in the art in view of the disclosure herein.

If the drill guide 210 has only one probe, the guide is pressed firmly against the skin in the area over where the bone is believed to be located. The probe 225 is pressed into the body with the knob 246. If the probe 225 does not contact bone firmly, the guide 210 is moved and the probe is re-inserted. Once contact has been established, the probe 225 may be removed from the bone 235 and the drill bit is preferably inserted through the same bore for drilling the hole. Once drilled, pressure is maintained on the drill guide 210 in the distal direction. Tissue will be restrained from occluding the hole by the serrations 234 located on the distal end 237 of the body 215.

Although this invention has been described in terms of certain preferred embodiments, other embodiments that are apparent to those of ordinary skill in the art in view of the foregoing are also within the scope of this invention. Accordingly, the scope of the invention is intended to be defined only by reference to the appended claims.

REFERENCES

[1] Pereyra, A. J.: A simplified surgical procedure for the correction of stress incontinence in women. West. J. Surg., 67:223, 1959.

[2] Stamey, T. A.: Endoscopic Suspension of the vesical neck for urinary incontinence in females: Report on 203 consecutive patients. Ann. Surg., 192:465, 1980.

[3] Raz, S.: Modified bladder neck suspension for female stress incontinence. Urology, 17:82, 1981.

[4] Leach, G. E.: Bone fixation technique for transvaginal needle suspension. Urology, 31:388, 1988.

[5] Gittes, R. F. and Loughlin, K. R.: No-incision pubovaginal suspension for stress incontinence. J. Urol. 138:568, 1987.

[6] Winter, C. C.: Peripubic urethropexy for urinary stress incontinence in women. Urology, 20:408, 1982.

[7] McKiel, C. F., Jr., Graf, E. C. and Callahan, D. H.: Marshall-Marchetti procedure: modification. J. Urol., 96:737, 1966.

[8] Hancock, R., Brandstetter, L. H. and Hodgins, T. E.: Transpubic suspension of the bladder neck for urinary incontinence. J. Urol., 123:667, 1980.

[9] Richmond, J. C., Donaldson, W. R., Fu, F. and Harner, C. D.: Modification of the Bankart reconstruction with a suture anchor: report of a new technique. Am. J. Sports Med., 19:343, 1991.

[10] Pederson, B., Tesoro, D., Wertheimer, S. J. and Coraci, M.: Mitek anchor system: a new technique for tenodesis and ligamentous repair of the foot and ankle. J. Foot Surg., 30:48, 1991.

We claim:

1. A bone anchor implantation device for directing a bone anchor at a selected site, comprising:
   a housing having at least a first and a second stationary and generally parallel probe channels;
   at least a first and a second generally parallel probes axially slidably extending through the housing the first and second probes being disposed in the first and second probe channels, respectively; and
   a guide channel extending through the housing generally parallel to the first and second probe channels, the guide channel being situated generally in between the first and second probe channels such that a line extending transversely between the first and second probe channels intersects at least a portion of the guide channel, wherein the guide channel has a slot extending through a wall of the guide channel and longitudinally throughout substantially the entire length of the guide channel.

2. A bone anchor implantation device as in claim 1, wherein at least the first probe is axially movable from a first proximal position to a second distal position.

3. A bone anchor implantation device as in claim 2, wherein the distal tip of the first probe is shielded within the housing when the probe is in the first position, and the distal tip of the first probe is exposed outside of the housing when the probe is in the second position.

4. A bone anchor implantation device as in claim 2, wherein at least the first and second probes are axially movable between the first proximal position and the second distal position.

5. A bone anchor implantation device as in claim 1, further comprising an actuator for moving the first probe between a first and second position.

6. A bone anchor implantation device as in claim 1, wherein the longitudinal axis of the guide channel is approximately equidistant from the longitudinal axes of each of the probes.

7. A bone anchor implantation device as in claim 2, further comprising a drill bushing extending through the guide channel.

8. A bone anchor implantation device as in claim 1, wherein said probe comprises an elongate solid wire.

9. A bone anchor implantation device as in claim 1, wherein said probe comprises an elongate hollow tube.

10. A bone anchor implantation device as in claim 1, wherein said probes have sufficient axial integrity to penetrate a bone, whereby said housing is maintained in a stable position.

11. A method of percutaneously positioning a bone anchor implantation device over an unexposed bone, comprising the steps of:

provviding a bone anchor implantation device of the type comprising a housing, at least two axially extendable probes within the housing, said probes being extendable from a retracted position to an extended position, and a guide channel extending through the housing;

positioning the guide channel over the unexposed bone;

advancing the first probe through a first tissue path until the first probe contacts a first side of the unexposed bone;

advancing the second probe through a second tissue path until said second probe contacts said first side of the unexposed bone; and if either one of the probes does not contact the unexposed bone, retracting at least that probe from the extended position to the retracted position, adjusting the position of the bone anchor implantation device, and then reextending at least that probe through a third tissue path until both probes contact the unexposed bone to assure that the guide channel is properly positioned over the unexposed bone.

12. A bone anchor implantation device for directing a bone anchor at a selected site, permitting introduction of the bone anchor through tissue and into a bone, comprising:

a unitary housing;

a textured soft tissue restraining structure on a distally facing tissue contacting surface of the housing;

at least a first and a second generally parallel probes slidably extendable through the housing, said first and second probes being disposed in a first and a second probe channels, respectively; and a guide channel extending through the housing generally parallel to the first and second probe channels, the guide channel having a diameter which is larger than the diameter of the first and second probe channels so that the bone anchor can be advanced into the bone through the guide channel.

13. A bone anchor implantation device as in claim 12, wherein the soft tissue restraining structure comprises serrations on the distally facing tissue contacting surface.

14. A bone anchor implantation device as in claim 13, wherein the soft tissue restraining structure comprises a plurality of generally parallel serration on the distally facing tissue contacting surface.

15. A bone anchor implantation device as in claim 12, further comprising a generally transversely extending handle attached to the housing.

16. A bone anchor implantation device as in claim 12, further comprising a bone anchor installation tool removably positioned in the guide channel and a bone anchor releasably secured to the bone anchor installation tool.

17. The method of claim 11, wherein the step of positioning the guide channel over the unexposed bone comprises positioning the guide channel over a pubic bone.

18. The method of claim 11, further comprising the step of advancing a bone anchor through the guide channel to implant the bone anchor into the unexposed bone.

* * * * *